US008435465B2

(12) United States Patent
Sundaram et al.

(10) Patent No.: US 8,435,465 B2
(45) Date of Patent: May 7, 2013

(54) MICROFLUIDIC BIOLOGICAL EXTRACTION CHIP

(75) Inventors: Shivshankar Sundaram, Madison, AL (US); Balabhaskar Prabhakarpandian, Madison, AL (US); Kapil Pant, Huntsville, AL (US); Yi Wang, Madison, AL (US)

(73) Assignee: CFD Research Corporation, Huntsville, AL (US)

( * ) Notice: Subject to any disclaimer, the term of this patent is extended or adjusted under 35 U.S.C. 154(b) by 615 days.

(21) Appl. No.: 12/263,911

(22) Filed: Nov. 3, 2008

(65) Prior Publication Data
US 2010/0112667 A1 May 6, 2010

(51) Int. Cl.
*A61J 1/06* (2006.01)
(52) U.S. Cl.
USPC ............ 422/554; 422/50; 422/500; 422/502; 422/527; 422/534; 422/535; 422/559; 422/243; 422/255; 422/261; 435/243; 435/259; 435/306.1; 435/173.4; 435/173.5; 435/173.6; 435/173.7; 436/43; 436/514
(58) Field of Classification Search ............ 422/50, 422/500–502, 527, 534, 535, 547, 554, 559, 422/243, 255, 261; 435/243, 259, 306.1, 435/173.1–173.9; 436/43
See application file for complete search history.

(56) References Cited

U.S. PATENT DOCUMENTS

| | | | |
|---|---|---|---|
| 5,707,799 A | 1/1998 | Hansmann et al. | |
| 6,103,199 A | 8/2000 | Bjornson et al. | |
| 6,106,779 A * | 8/2000 | Buechler et al. | 422/417 |
| 6,287,831 B1 * | 9/2001 | Tai et al. | 435/173.7 |
| 6,878,540 B2 * | 4/2005 | Pourahmadi et al. | 435/287.2 |
| 6,880,576 B2 * | 4/2005 | Karp et al. | 137/806 |
| 7,014,747 B2 | 3/2006 | Cummings et al. | |
| 7,160,423 B2 | 1/2007 | Chien et al. | |
| 7,169,277 B2 | 1/2007 | Ausserer et al. | |
| 7,204,923 B2 * | 4/2007 | Cummings | 204/547 |
| 2002/0160518 A1 | 10/2002 | Hayenga et al. | |
| 2004/0058423 A1 | 3/2004 | Albritton et al. | |
| 2005/0133371 A1 | 6/2005 | Timperman et al. | |
| 2006/0110294 A1 * | 5/2006 | Engstrom et al. | 422/100 |
| 2007/0031283 A1 * | 2/2007 | Davis et al. | 422/58 |
| 2007/0134809 A1 | 6/2007 | Cho et al. | |

FOREIGN PATENT DOCUMENTS

| | | | |
|---|---|---|---|
| JP | 01141582 A * | 6/1989 | |
| WO | WO 2006128098 A2 * | 11/2006 | |
| WO | WO 2007106579 A2 * | 9/2007 | |

OTHER PUBLICATIONS

Chang, Chih-Chang and Yang, Ruey-Jen, Electrokinetic mixing in microfluidic systems, 2007, Microfluidics and Nanofluidics, vol. 3, pp. 501-525.*
Lu et al., A microfluidic electroporation device for cell lysis, 2005, Lab on a Chip, vol. 5, pp. 23-29.*
Martinez et al., Numerical analysis of microelectrodes for cell electrokinetic applications, 2008, Journal of Applied Physics, vol. 104, pp. 064512:1-6.*

* cited by examiner

*Primary Examiner* — Melanie Y Brown
*Assistant Examiner* — Erik B Crawford
(74) *Attorney, Agent, or Firm* — Maschoff Brennan (57) ABSTRACT

A microfluidic cartridge for isolating biological molecules having a capture chamber containing functionalized solid supports maintained in a fluidized state provides reduced pressure drops and bubble formation during microfluidic extraction. The cartridge may include an electric field lysis chamber and/or a chemical lysis chamber. The electric-field lysis chamber may comprise an electrically insulating structure arranged between two opposing planar electrodes.

20 Claims, 9 Drawing Sheets

| Operation | 01 | 02 | 03 | 04 | 05 | 06 | 07 | 08 | 09 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|
| 1. Prime entire card | O | x | O | x | O | x | O | x | x | O | O | x | x | O | O | x | x | O | O | O | x | O | O | O |
| 2. Load cell solution | x | O | x | x | x | x | x | x | x | x | x | O | x | x | x | x | x | x | x | x | x | x | x | x |
| 3. Load lysis soln | x | x | x | O | x | x | x | x | x | x | x | x | x | x | x | O | x | x | x | x | x | x | x | x |
| 4. Load elution buffer | x | x | x | x | x | x | x | x | x | x | O | x | x | x | x | x | x | x | x | O | x | x | x | x |
| 5. Load nuclease soln | x | x | x | x | x | O | x | x | O | x | x | x | x | x | x | x | x | x | x | x | x | x | x | x |
| 6. Load wash buffer | x | x | x | x | x | x | x | O | x | x | x | x | x | x | x | O | x | x | x | x | x | x | x | x |
| 7. Load beads | x | x | x | x | x | x | x | x | x | x | x | x | x | x | x | x | O | x | x | x | x | x | x | x |
| 8. Reagent-based cell lysis | O | x | O | x | x | x | x | x | x | x | x | x | O | O | x | x | x | O | x | x | x | O | x | x |
| 9. Field driven cell lysis | O | x | x | x | x | x | x | x | x | x | x | x | O | x | x | x | x | O | x | x | x | O | x | x |
| 10. Mix in contacting loops | x | x | O | x | x | x | x | x | x | x | x | x | x | O | x | x | x | O | x | x | x | x | x | O |
| 11. Mix in buffer chamber | x | x | x | x | x | x | x | x | x | x | x | x | x | x | x | x | x | O | x | x | x | x | x | O |
| 12. Wash 1 | x | x | x | x | x | x | O | x | x | x | x | x | x | x | x | x | x | O | O | x | x | x | x | x |
| 13. Nuclease wash | x | x | x | x | O | x | x | x | x | O | x | x | x | x | x | x | x | O | x | x | x | x | x | x |
| 14. Wash 2 | x | x | x | x | x | x | O | x | x | x | x | x | x | x | x | x | O | O | x | x | x | x | x | x |
| 15. DNA elution | x | x | x | x | x | x | x | x | x | x | O | x | x | x | x | x | x | O | x | x | O | x | x | x |
| 16. Mixing | x | x | x | x | x | x | x | x | x | x | x | x | x | x | x | x | x | O | x | x | x | x | x | O |
| 17. Product to storage | x | x | x | x | x | x | x | x | x | O | x | x | x | x | x | x | x | x | O | x | O | O | x | x |

MICROFLUIDIC BIOLOGICAL EXTRACTION CHIP

STATEMENT REGARDING FEDERALLY SPONSORED RESEARCH OR DEVELOPMENT

The U.S. Government has rights in this invention under Contract No. NNJ05JA04C.

CROSS-REFERENCE TO RELATED APPLICATIONS

Not Applicable

INCORPORATED-BY-REFERENCE OF MATERIAL SUBMITTED ON A COMPACT DISC

Not Applicable

BACKGROUND OF THE INVENTION

1. Field of the Invention

The present invention is a microfluidics-based cartridge for automated extraction of biological molecules from cells, spores, virions, their lysates, and other biological samples. The present invention is capable of isolating nucleic acids, proteins, and other biological macromolecules from less than 10,000 cells in 30 minutes.

2. Description of Related Art

Microfluidic apparatus and methods for the lysis of cells and/or separation of selected lysate components are known in the art. U.S. Pat. No. 6,287,831 B1 to Tai et al. discloses a cell lysis device in which micromachined electrodes spaced less than 100 micrometers apart on a silicon substrate are used to lyse cells. US 2007/0134809 (Cho et al.) discloses a microfluidic device for the concentration and lysis of cells or viruses in which lysis is accomplished by radiating magnetic beads in a reaction chamber with a laser. US 2004/0058423 A1 (Albritton et al.) discloses an apparatus for sequential lysis of selected adherent cells in which a single electric pulse of between 10 milliseconds and 10 microseconds is used to lyse cells and lysate is transferred into a microcollection device. U.S. Pat. No. 7,169,277 B2 to Ausserer et al. discloses a device that separates sample materials into different fractions using a combination of bulk flow for loading samples and electrophoretic separation of sample materials.

A microfluidic cartridge and associated method for selective lysis of and extraction of DNA from cell mixtures is disclosed in US 2005/0064598 A1 (Yuan et al.). The microfluidic differential extraction cartridge selectively lyses one of at least two populations of cells in a mixed sample using sonication at frequencies capable of lysing on cell type and not another. The differential extraction is based on the selective lysis of one cell type over another using, for example, sonication to selectively lyse one cell type and chemicals or heat to lyse a second cell type. The cartridge comprises a sample input chamber, a sonication lysis chamber, a means for separating lysed cells from intact cells, and a collection vessel to collect cell lysate. An additive, such as glass beads or chemicals can be added to the sonication chamber before cell lysis. The cartridge may comprise a mixing chamber to add and mix a solution into a cell lysate and a purification chip to purify and concentrate nucleic acid from the cell lysate.

The utility of existing microfluidic systems for cell lysis and isolation is, in some cases, limited due to high internal pressure drops required to achieve acceptable flow rates, capture and elution times, and bubble formation. The present invention overcomes these limitations by providing a capture chamber containing beads that bind the target species to be captured wherein the beads are maintained in a fluidized state.

BRIEF SUMMARY OF THE INVENTION

In one aspect, the present invention is a microfluidic extraction cartridge and method comprising a bead-based capture and elution chamber comprising a loosely packed, fluidized solid supports, such as beads. By "loosely packed, fluidized", it is meant that the solid supports are not static, as in a packed column, but rather free to move relative to one another such that the supports may flow like a liquid. The chamber containing the solid supports and the chamber inlets and outlets are configured in a way that increases reagent contact and reduces bubble formation relative to existing devices. Electrokinetic mixing can be incorporated to reduce mixing, capture, and elution times.

Compared to capture chambers of the prior art containing packed beads or porous filters for binding target species, the present capture chamber provides for a lower pressure drop across the chamber. The shape of the capture chamber and relative positions of the inlet to and outlet from the chamber may be designed to reduced bubble formation and maximized contact between solution and beads. For instance, a disc shaped capture chamber is preferred to minimize bubble formation and maximize contact between fluid and the beads.

In another aspect, the present invention is an electric field lysis chamber comprising embedded, insulating structures between two parallel, flat electrodes used to generate strong electric field gradients in the gaps between the insulating structures. This configuration simplifies and reduces the cost of manufacture compared to known microfluidic electric field lysis chambers. A wedge electrode design is known in which the electrode surfaces form wedge shapes to generate electric fields having local field intensities capable of lysing cells. Patterned electrode structures, while being the most direct way of attaining the large electric fields needed for cell lysis, introduce significant complexities related to the manufacturing process, biofouling, bubble formation, and electrochemical reactions. The electric field lysis chamber of the present invention does not require metal electrodes having patterned electrode geometries. Instead, the electric field originates at the surface of electrodes and passes through the insulating structures, leading to sustained, strong electric fields across the flow path and efficient lysis.

In yet another aspect, the present invention is an extraction cartridge comprising one, two, or more lysis chambers and a capture chamber comprising fluidized beads. The beads (magnetic or non-magnetic) are functionalized to bind to nucleic acids or other target biomolecules and are held in the capture chamber by bead containment membranes. The beads are maintained in a fluidized state by using electric fields generated using electrodes located in the capture chamber. In addition to fluidizing the beads, the electrokinetic flows improve the contacting and mixing between the beads and the target, thereby reducing the contacting time capture onto and elution from the bead surface.

BRIEF DESCRIPTION OF THE SEVERAL VIEWS OF THE DRAWINGS

FIGS. 9 (A) and (B) show side cross-section and exploded perspective views of an electric field lysis chamber comprising a porous, electronically insulating gasket separating two planar electrodes.

DETAILED DESCRIPTION OF THE INVENTION

Figure 1:
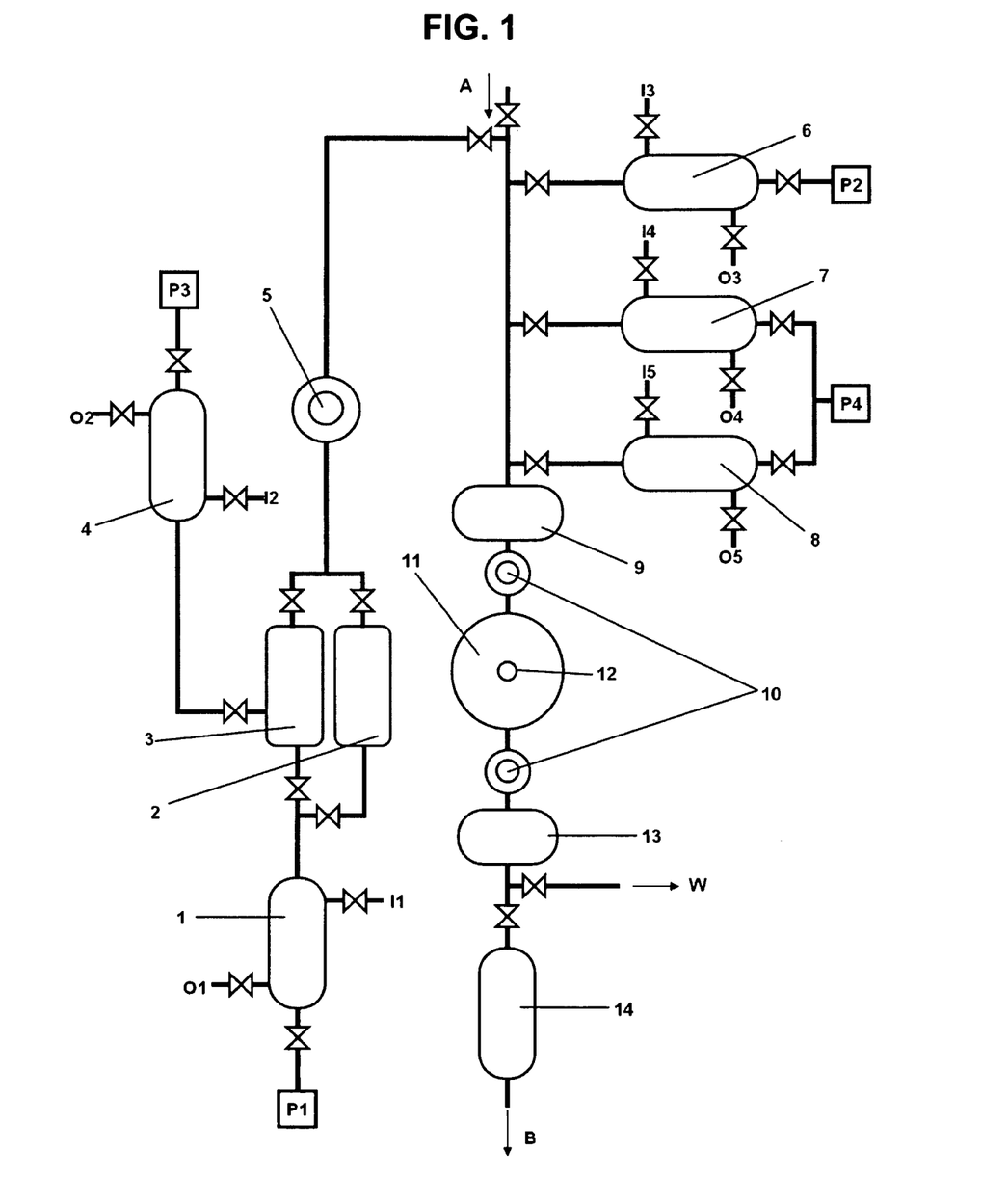
FIG. 1 is an idealized layout of a preferred embodiment of a microfluidic extraction cartridge with lysis and capture chambers and loops labeled.

FIG. 1 illustrates the layout of a first embodiment of a microfluidic extraction cartridge. The cartridge is configured for the extraction of nucleic acids from cells or cell lysate but other embodiments may be configured for the extraction of protein, protein fractions, or other cellular contents by altering the binding properties of the beads used for molecular capture. Additionally, the lysis chambers may be configured and operated to disrupt other sources of DNA or RNA such as viruses or bacterial or fungal spores. Table 1 lists the structural elements identified in FIG. 1.

TABLE 1

| | |
|---|---|
| 1 | Sample Loop |
| 2 | Electric Field Lysis Chamber |
| 3 | Chemical Lysis Chamber |
| 4 | Chemical Lysis Reagent Loop |
| 5 | Lysate Filter Membrane |
| 6 | Wash Buffer Loop |
| 7 | Nuclease Solution Loop |
| 8 | Elution Buffer Loop |
| 9 | Contacting Loops |
| 10 | Bead Containment Membranes |
| 11 | Capture Chamber |
| 12 | Bead Injection Port |
| 13 | Buffer Chamber |
| 14 | Product Storage Chamber |
| P1 | Pump 1 |
| P2 | Pump 2 |
| P3 | Pump 3 |
| P4 | Pump 4 |

Sample Loop 1 may be loaded with cells, spores, virions or other lysable sources of nucleic acids or other biomolecules suspended in buffer solution. Two lysis chambers are present in the preferred embodiment of the invention; a Chemical Lysis Chamber and an Electric Field Lysis Chamber. The term chemical lysis is meant to include enzymatic as well as purely chemical lysis. Electric Field Lysis Chamber 2 and Chemical Lysis Chamber 3 may be arranged in parallel or in series, and may be both used for the lysis of the same sample, used simultaneously for lysis of the same sample, or used at different times to lyse different samples. In embodiments having a second sample loop, different samples may be lysed simultaneously in the two lysis chambers. If chemical lysis is used, reagents are loaded into Chemical Lysis Reagent Loop 4 for delivery to Chemical Lysis Chamber 3.

Lysate Filter Membrane 5 traps cell lysate debris and prevents clogging of the downstream channels and chambers due to the presence of the debris. Additional lysate filters may be arranged in series and/or in parallel to facilitate processing of multiple samples. Contacting Loops 9 allow cell lysate to interact with nucleases delivered from Nuclease Solution Loop 7. For example, DNAse may be delivered from Nuclease Solution Loop 7 to degrade DNA for isolation of RNA or RNAse may be delivered from Nuclease Solution Loop 7 to degrade RNA for isolation of DNA. Other embodiments may include one or more of DNAse, RNAse or protease loops, for example, depending on the type of molecule being isolated.

Capture Chamber 11 is loaded through Bead Injection Port 12 with beads (magnetic or non-magnetic) functionalized to bind to nucleic acids or other target biomolecules and maintained in a fluidized state. The beads are held in the capture chamber by Bead Containment Membranes 10 and are maintained in a fluidized state by fluidic flow or by using electric fields generated using electrodes located in the capture chamber. Bead Containment Membranes 10 are preferably asymmetric membranes having a smaller pore size (e.g., 0.8 µm) on the bead side and a larger pore size (e.g., 10 µm) on the port side. The surface area of the membranes exposed to fluid flow is preferably maximized to minimize fluidic resistance and each membrane is preferably supported by a structure incorporated into each membrane mount to prevent membrane collapse.

The Capture Chamber 11 lacks sharp corners and contains fluidized beads, functionalized to bind selected targeted cellular contents such as RNA, DNA, and proteins. In one preferred embodiment, the capture chamber is circular in shape. Staggered saw-tooth electrodes may be placed on the floor of the capture chamber and energized with ±15V at alternate electrode strips to actively mix chamber contents. Alternatively, the chamber contents may be mixed actively by using bidirectional pumping by connecting a external fluidic pump to the extraction cartridge at access port 20. Wash Buffer Loop 6 and Elution Buffer Loop 8 provide buffer solutions for washing the target biomolecules bound to the beads and eluting nucleic acids from the beads. The purified biomolecule is stored in the Product Storage Chamber 14 until removed from the cartridge using an access port 15.

An extraction cartridge having the design shown in FIG. 1 may used for the extraction and purification of RNA, DNA, protein, or other biological material from suspended cells, viruses, spores, or other biological samples. Isolation is performed using small volumes of sample of typically between 0.1 and 2 ml of cell suspension. Reagents and conditions selected based on the material being isolated and the sample from which it is isolated.

Preferably, the entire cartridge is prewashed with a BSA solution or other solution before initial use to prevent nonspecific binding between the material(s) being isolated and the material from which the cartridge is manufactured. The cartridge may be reused after washing. Isolated product, once eluted form the beads, may be stored for later use or transported directly via microfluidic channels or other means to other devices or instruments for analysis.

Figure 2:
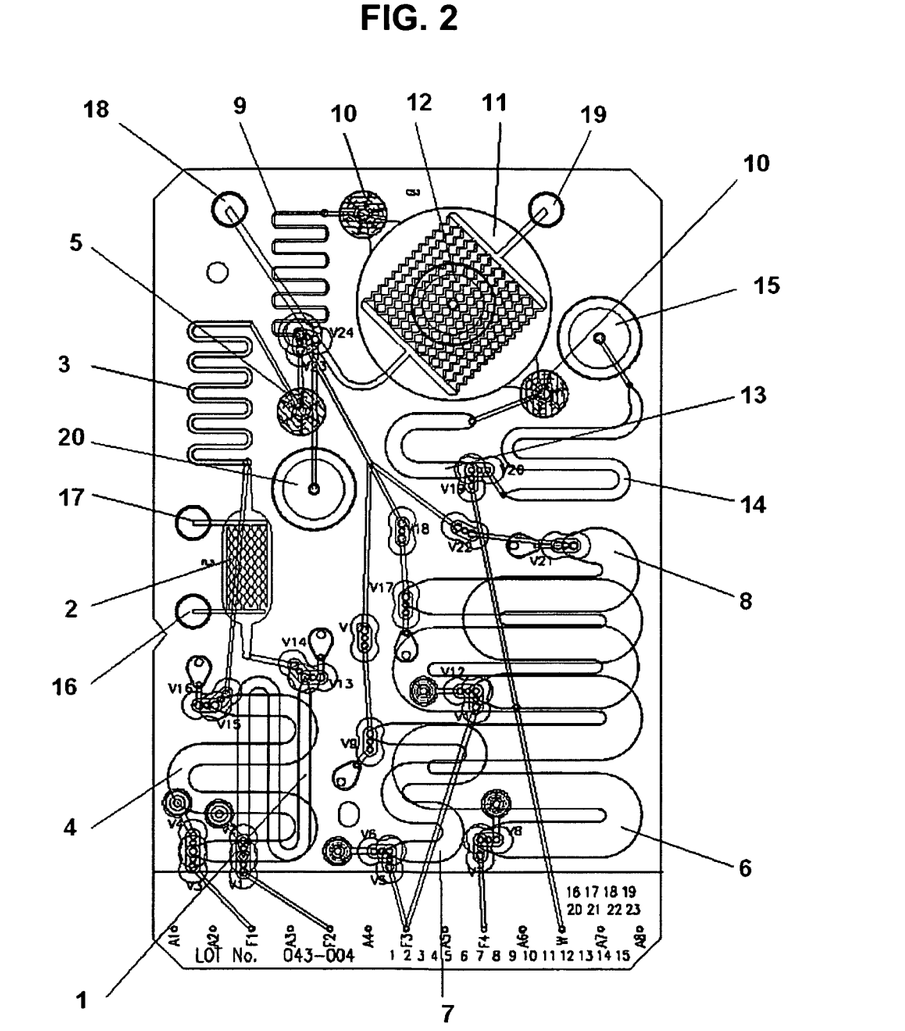
FIG. 2 is a CAD drawing of a preferred embodiment of a microfluidic extraction cartridge according to the present invention with lysis and capture chambers and loops labeled.

FIG. 2 is a CAD drawing corresponding to the extraction cartridge schematic shown in FIG. 1. In addition to the elements shown in FIG. 1, port 15 for removal of isolated nucleic acid is shown. Anode 16 and Cathode 17 are connected to electrodes in the Electric Field Lysis Chamber 2. Anode 18 and Cathode 19 are connected to electrodes located in the Capture Chamber 11 and are used to maintain the beads in a fluidized state. The beads are fluidized using electrokinetic phenomena obtained by application of an applied voltage at the Anode 18 and Cathode 19, which generate localized eddies. In addition to fluidizing the beads, the electrokinetic flows improve the contacting and mixing between the beads and the target, thereby reducing the contacting time for capture onto and elution from the bead surface.

An extraction cartridge having the configuration shown in FIG. 1 was manufactured using layers of polyethylene terephthalate film laminated with 2 mil thick 3 M 300LSE® acrylic adhesive. Alternatively, extraction cartridges may be constructed of other suitable substrates including plastics, glass, polymers, etc. and methods used to manufacture microfluidic devices. One or more layer of acrylic is used for structural strength and to provide volume for fluid storage.

Figure 3:
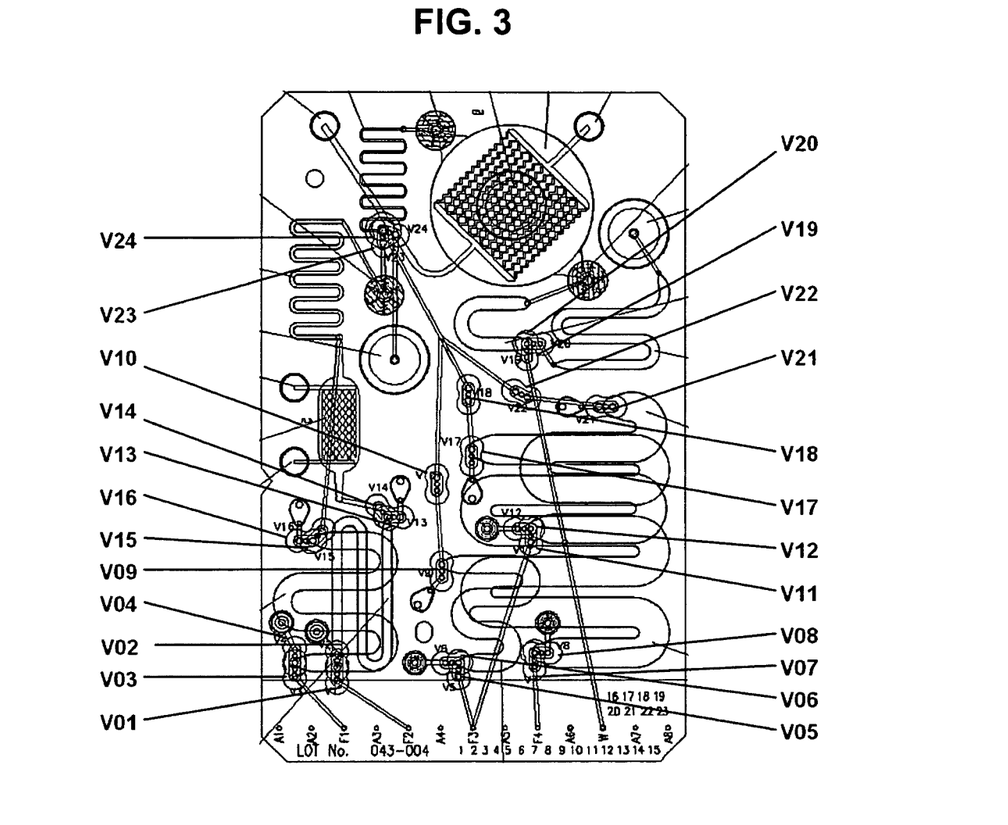
FIG. 3 is a CAD drawing of a preferred embodiment of a microfluidic extraction cartridge according to the present invention with valves labeled.

The cartridge shown in FIG. 1 contains 24 pneumatically controlled valves that, in this embodiment, are designed to interface to a microFlow™ μHydro™ manifold. FIG. 3 shows the CAD drawing in FIG. 2 with the all the valves clearly labeled. The valves in this instance are manufactured from a thin urethane film. Flow between the various components of the extraction cartridge is controlled by a combination of pressure and vacuum applied at the manifold to regulate the opening and closing of the valves. In this embodiment, the fluidic pumps are connected to the cartridge via the interface of the microFlow™ μHydro™ manifold. The pump connections designated as P1, P2, P3 and P4 are shown in FIG. 1.

Figure 4:
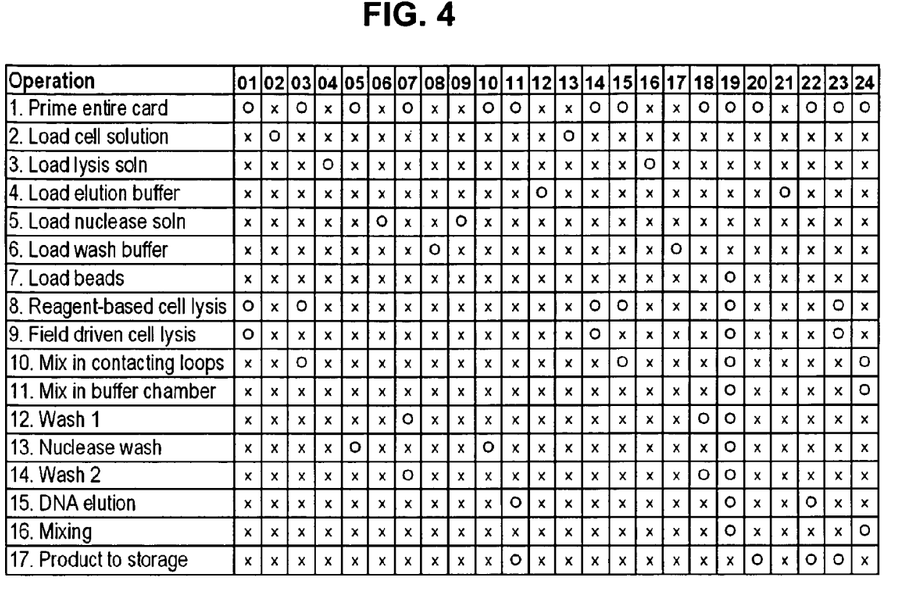
FIG. 4 is a table showing the valve operation logic of a preferred embodiment of a microfluidic extraction cartridge.

FIG. 4 shows the valve operation used during the lysis and extraction of nucleic acids from cells using the embodiment of the invention shown in FIG. 1 and FIG. 2. The valve numbers correspond to the valve numbers shown in FIG. 3 with "X" indicating that the valve is closed and "o" indicating that the valve is open. Each of the functional components including loops, chambers, and valves are connected via microfluidic interconnects.

Example of Cartridge Operation Comprising Two Lysis Chambers:

The operation of the extraction cartridge for RNA purification from cell cultures, comprising of two lysis chambers arranged in parallel is exemplified as follows:

Prime the Card

Prime the card using RNase free ultra pure deionized (DI) water, using all four pumps.

Load the Card:
1. Load Cell Solution in Sample Loop,
2. Load Lysis Reagent in Chemical Lysis Reagent Loop,
3. Load Elution Buffer in Elution Buffer Loop,
4. Load DNAse Solution in Nuclease Solution Loop,
5. Load Wash Buffer in Wash Buffer Loop,
6. Load Beads in Capture Chamber.

Activate the Card
1. Cell Lysis: Cell solution is pushed from the Sample Loop 1 into one of the two lysis chambers. If Electric Field Lysis Chamber 2 is used, the electrodes are activated. If Chemical Lysis Chamber 3 is used, lysis reagent from Chemical Lysis Reagent Loop 4 is pushed into the Chemical Lysis Chamber 3. The incoming cell solution stream is directed to feed the lysis chamber in use. Alternatively, the cell solution stream may be split into two using valves to feed to the both lysis chambers arranged in parallel. The exiting stream from the lysis chambers are rejoined (via valved lines) and passed through the cell debris filter (pore size ~1 μm). Excess fluid in either scenario is routed to off-chip waste.

2. RNA Capture: The filtered cell lysate is contacted with binding buffer via the syringe pump access port 20 and the lysate and binding buffer solution is routed to the Capture Chamber 11, which is pre-loaded with functionalized beads. RNA and DNA in the filtered cell lysate bind to the beads. The binding may be enhanced using either electrokinetic mixing by energizing electrodes located in the Capture Chamber 11, or, hydrodynamic mixing using bidirectional pumping enabled by the syringe pump located at the access port 20. In the latter case, the Buffer Chamber 13 is used to modulate the amplitude of bidirectional pumping.

3. Wash 1: Wash buffer is pumped from the Wash Buffer Loop 6 into the Capture Chamber 11 to displace the binding buffer and flush out unbound RNA/DNA/protein. Excess fluid is routed to off-chip waste.

4. DNase Wash: DNAse solution is pumped from the Nuclease Solution Loop 7 is flowed through the Capture Chamber 11 to degrade DNA bound on the beads. Excess fluid is routed to off-chip waste.

5. Wash 2: Wash buffer is pumped from the Wash Buffer Loop 6 into the Capture Chamber 11 to displace the DNase solution and flush out any degraded DNA. Excess fluid is routed to off-chip waste.

6. RNA Elution: Elution buffer is pumped from the Elution Buffer Loop 8 into the Capture Chamber 11 to elute RNA bound on beads. RNA elution may be enhanced using either electrokinetic or hydrodynamic mixing. The exit stream from the Capture Chamber 11 at the end of RNA elution step is routed to a Product Storage Chamber 14.

Exemplary Chamber and Loop Volumes:
Chambers:
Electric Field Lysis Chamber: 10 μl
Chemical Lysis Chemical: 50 μl
Capture Chamber: 100 μl
Storage Loops:
Sample Loop: 200 μl
Chemical Lysis Reagent Loop: 400 μl
Elution Buffer Loop: 200 μl
Nuclease Solution Loop: 400 μl
Wash Buffer Loop: 1 ml
Lysis Chamber(s):

The extraction cartridge may contain one, two, or more than two lysis chambers. Each lysis chamber may be a chemical lysis chamber or an electric field lysis chamber. In a preferred embodiment, the cartridge comprises one electric and one chemical lysis chamber to allow the user to select from electric lysis, chemical lysis, or both.

Figure 5:
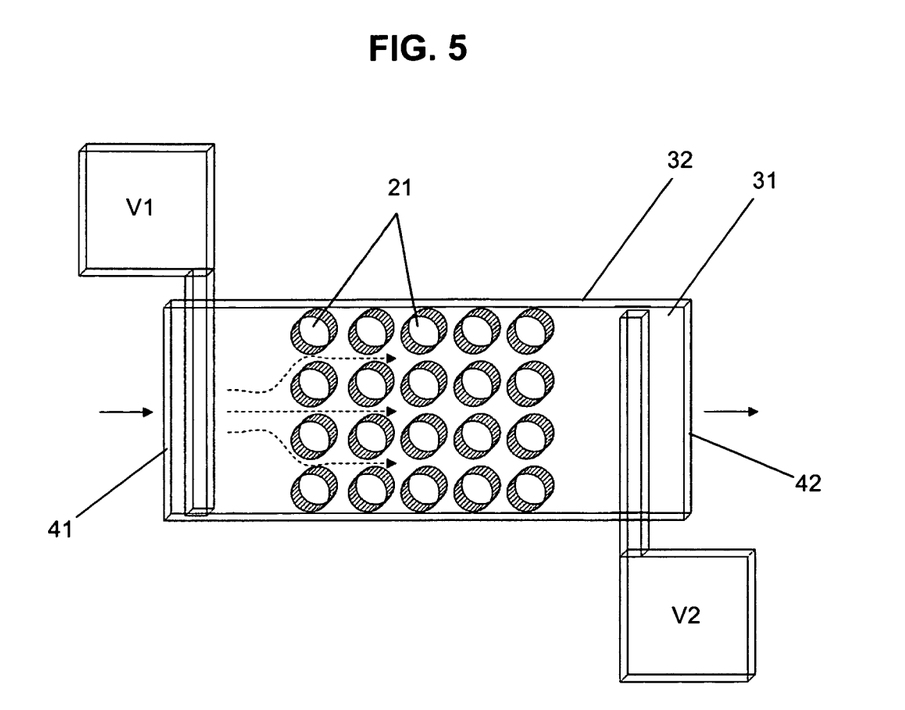
FIG. 5 shows a top view of a diagram of an electric field lysis chamber comprising insulating posts separating two planar electrodes.
Figure 6:
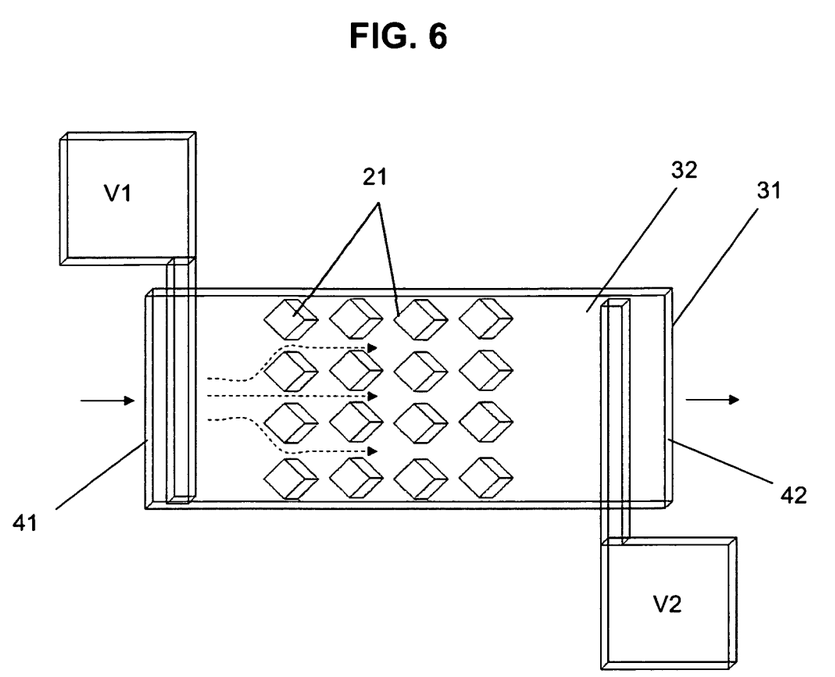
FIG. 6 shows a top view of a diagram of an electric field lysis chamber comprising cubic-packed insulating posts between two planar electrodes.
Figure 7:
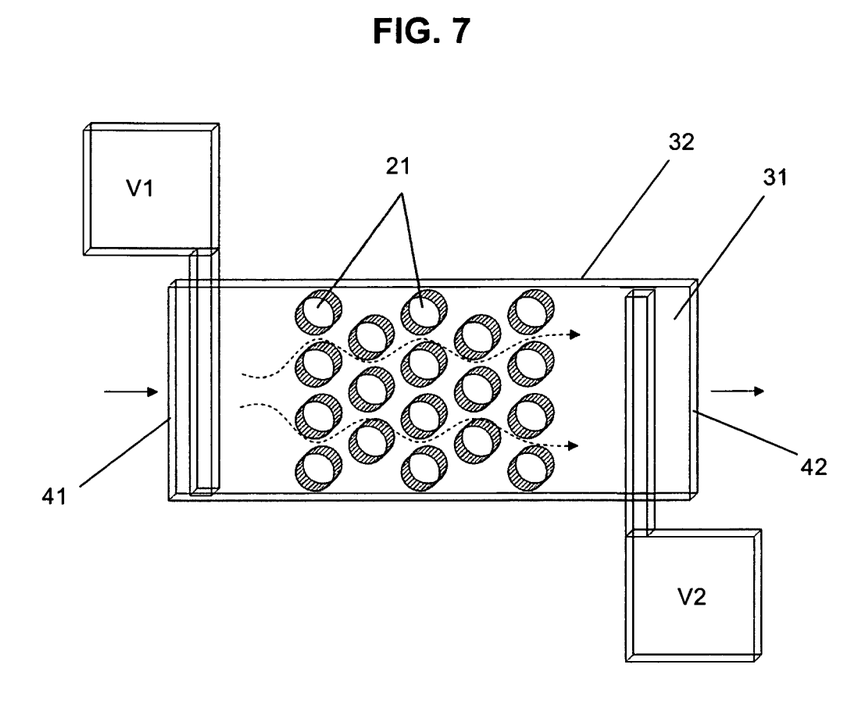
FIG. 7 shows a top view of a diagram of an electric field lysis chamber comprising hex-packed insulating posts between two planar electrodes.

FIG. 5 is a schematic of an Electric Field Lysis Chamber 2 wherein voltage is applied between two electrodes 31 and 32 via connection pads $V_1$ and $V_2$ arranged on either side of an array of insulating posts 21. In this embodiment, the insulating posts have a cylindrical shape and are arranged perpendicularly to the electrodes 31 and 32. Arrows indicate the flow of cell-containing solution into the chamber though inlet 41 and lysate flow exiting the chamber though outlet 42. The insulating posts cause the electric field between the electrodes to form areas of high and low electric field. FIG. 6 and FIG. 7 show two exemplary embodiments of insulation post arrays with quadrilateral and circular cross sections. The posts within an array may be packed cubically to form a square array as in FIG. 6 or hex-packed to form a staggered array as in FIG. 7. The insulating posts may be spaced between 10 μm and 100 μm apart and extend vertically from the floor to the ceiling of the lysis chamber to enable high electric field creation throughout the volume of the chamber. In this example the spacing between posts is 40 μm.

Figure 8:
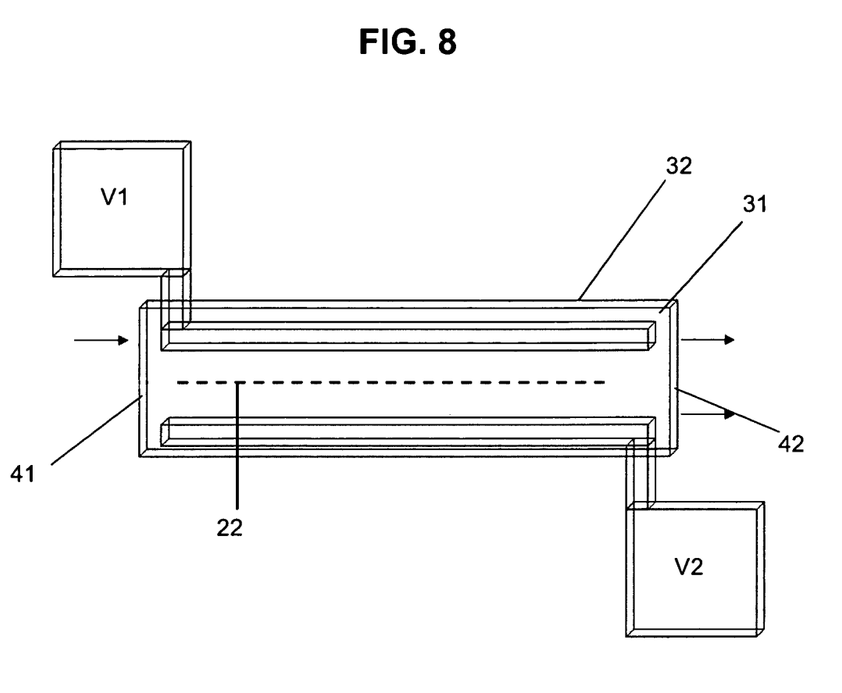
FIG. 8 is a diagram of an electric field lysis chamber comprising a porous, electronically insulating gasket separating two planar electrodes.
Figure 9:
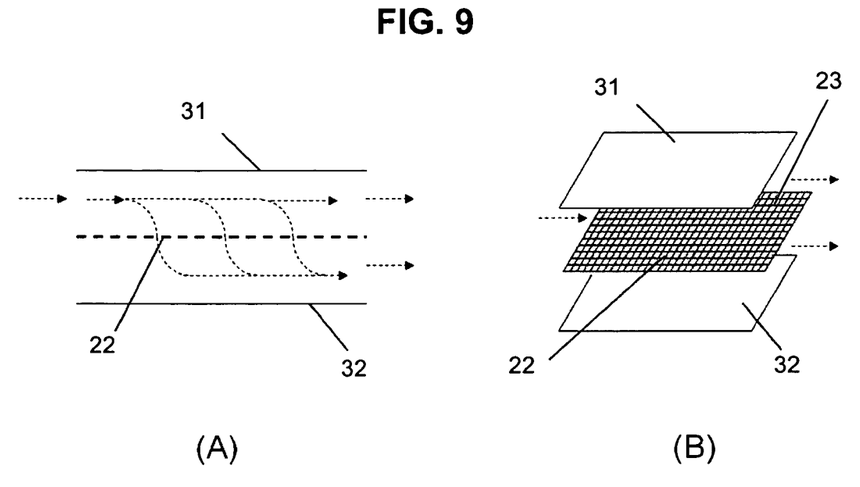

FIG. 8 illustrates an Electric Field Lysis Chamber 2 chamber design in which a porous, electrically insulating mesh 22 is sandwiched between planar electrodes 31 and 32 located at the top and bottom of the chamber. The insulating mesh may also act as a sieve to separate cell debris from cell lysate. FIGS. 9(A) and 9(B) show side cross-section and perspective views corresponding to FIG. 8, including enlarged strands 23 of the electrically insulating mesh that form spacers in contact with the electrodes and allow the flow of liquid through the lysis chamber. Cells may be lysed using voltages of 5 Volts or more at a frequency of 10 kHz or greater. In this arrangement, it is advantageous for the electrodes be made out of optically transparent materials to facilitate visualization of the lysis chamber. For example, the electrodes may be made of optically transparent Indium-Tin-Oxide (ITO) deposited on glass or plastic forming the top and bottom surfaces of the lysis chamber.

The exemplary embodiment described herein may be altered in a variety of ways without departing from the invention including, but not limited to: altering the geometries, dimensions, and volumes of microfluidic components; relocating chamber entry and exit ports; and the inclusion of electrodes configured to provide active electrokinetic mixing and/or cleaning elements in one or more of the chambers. The Nuclease Solution Loop 7 may be replaced by a protease loop or protease inhibitor loop, for example, depending on the type of molecule to be isolated.

RNA, DNA, protein, carbohydrates, glycoproteins, metabolic intermediates, and other biomolecules are not always derived from samples that require the disruption or lysing of cells. In these cases, an embodiment of the invention need not include electric field or chemical lysis chambers. For example, a microfluidic extraction cartridge comprising the components of the cartridge shown in FIGS. 1 and 2 may be made but without the chemical lysis chamber 3, electric field lysis chamber 2, and chemical lysis reagent loop 4. Sample, after being loaded into the Sample Loop 1 would move to the Capture Chamber 11 with or without passing through contacting loops containing reagents for degrading unwanted molecules or preventing the degradation of the molecules to be isolated.

What is claimed is:

1. A microfluidic cartridge for isolating biological molecules from a liquid sample comprising:
    a sample loop configured for receiving a sample;
    an electric field lysis chamber downstream from the sample loop, the electric field lysis chamber having insulating members between lysing electrode members, wherein the insulating members and lysing electrode members are cooperatively configured to lyse cells to produce cell lysate;
    a capture and elution chamber having an inlet and an outlet and containing a fluidized solid support, the fluidized solid support including beads that are fluidized in response to electric fields, the inlet being downstream from the electric field lysis chamber;
    a first electrode operably coupled to one side of the capture and elution chamber and a second electrode operably coupled to an opposite side with respect to the first electrode, wherein the first electrode and second electrode are cooperatively configured with the beads of the fluidized support such that activation of these electrodes fluidize the fluidized solid support;
    an inlet conduit fluidly coupled to the inlet of the capture and elution chamber and an outlet conduit fluidly coupled to the outlet of the capture and elution chamber;
    an inlet membrane located in the inlet conduit and an outlet membrane located in the outlet conduit and positioned such that the fluidized solid support is held within the capture and elution chamber; and
    pneumatically controlled valves controlling fluid flow into and out of the capture and elution chamber.

2. The microfluidic cartridge of claim 1, wherein the inlet and outlet membranes are asymmetric membranes.

3. The microfluidic cartridge of claim 1, wherein the shape of the capture and elution chamber is selected from the group consisting of a planar disc, an oval, a polygon, and a tear-drop.

4. The microfluidic cartridge of claim 1, wherein said first electrode and second electrodes configured as staggered sawtooth electrodes are located in the capture and elution chamber and configured to be energized with +/−15 V at alternate electrode strips, and said first and second electrodes are configured to cause electrokinetic mixing when a potential is applied to the first and second electrodes.

5. The microfluidic cartridge of claim 1, and further comprising:
    a wash buffer loop and wash buffer contact loop wherein the wash buffer loop is in fluid communication with the wash buffer contact loop and the wash buffer contact loop is in fluid communication with the inlet to the capture and elution chamber, the wash buffer loop including a wash buffer and/or a nuclease solution;
    an elution buffer loop in fluid communication with an elution buffer contact loop that is in fluid communication with the inlet to the capture and elution chamber; and
    an isolate storage chamber downstream of the outlet of the capture and elution chamber.

6. A microfluidic cartridge for isolating biological molecules from a liquid sample comprising:
    a capture and elution chamber having an inlet and an outlet and a fluidized solid support;
    an inlet conduit fluidly coupled to the inlet of the capture and elution chamber and an outlet conduit fluidly coupled to the outlet of the capture and elution chamber; and
    an electric field lysis chamber having an electric field lysis chamber inlet and an electric field lysis chamber outlet that is upstream of the inlet conduit, and having an first lysis electrode and second lysis electrode on opposing sides of the electric field lysis chamber with one or more insulating members sandwiched between the first and second lysis electrodes, wherein the electrically insulating material and first and second lysis electrodes are is configured to cause the formation of high and low electric fields capable of lysing cells to produce cell lysate when a potential is applied across the first and second lysis electrodes;
    a chemical lysis chamber upstream from the inlet of the capture and elution chamber; and
    a chemical lysis reagent loop fluidly coupled with the chemical lysis chamber.

7. The microfluidic cartridge of claim 6, wherein the insulating structure is a structure selected from the group consisting of a porous membrane, a web, and a mesh.

8. The microfluidic cartridge of claim 6, wherein the chemical lysis chamber is arranged in parallel with the electric field lysis chamber.

9. The microfluidic cartridge of claim 6, and further comprising:
    a cell sample intake well, a reagent contacting loop, a buffer contact loop, an isolate storage chamber for eluted biomolecules, a wash buffer loop, a reagent loop, an elution buffer loop, and a lysis reagent loop
wherein:
the cell sample intake well, electric field lysis chamber, reagent contacting loop, capture and elution chamber, elution buffer contact loop, and isolate storage chamber are in the recited sequence and successive fluid communication through microfluidic channels; and
the wash buffer loop, reagent loop, and elution buffer loop are in fluid communication with a microfluidic channel between the cell lysis chamber and the reagent contacting loop.

10. A method for isolating target biomolecules from a liquid sample using the microfluidic cartridge recited in claim 1 comprising the steps of:
loading the sample into the sample inlet of microfluidic cartridge comprising: a sample inlet, an isolate outlet, and a capture and elution chamber containing a fluidized solid support in fluid communication with the sample inlet and isolate outlet;
causing the liquid sample to move from the sample inlet into the capture and
allowing the target biomolecule to bind to the solid support in the capture and elution chamber; and
eluting the target biomolecules from the solid support on the capture and elution chamber to recover the isolated target biomolecules.

11. The method according to claim 10, wherein the liquid sample comprises cells, spores, and/or virions and the microfluidic cartridge further comprises a cell lysis chamber and wherein the method further comprises the step of:
causing the liquid sample to move from the sample inlet into the cell lysis chamber and lysing the cells, spores, and/or virions before causing the sample to move into the capture and elution chamber.

12. A microfluidic cartridge for isolating biological molecules from a liquid sample comprising:
a) a cell sample intake well having an sample outlet;
b) an electric field cell lysis chamber having a lysis chamber inlet fluidly coupled with the sample outlet and having a lysis chamber outlet;
c) a reagent contacting loop having a contacting loop inlet fluidly coupled with the lysis chamber outlet and having a contacting loop outlet;
d) a capture and elution chamber having a chamber inlet fluidly coupled to the contacting loop outlet and having a chamber outlet and containing a fluidized solid support;
e) an elution buffer contact loop having an elution buffer contact loop inlet fluidly coupled with the chamber outlet and having an elution buffer contact loop outlet;
f) a storage chamber for eluted molecules having a storage chamber inlet fluidly coupled to the elution buffer contact loop outlet and having an access port;
g) a wash buffer loop fluidly coupled with the contacting loop;
h) a reagent loop fluidly coupled with the contacting loop;
i) an elution buffer loop fluidly coupled with the contacting loop; and
j) a lysis reagent loop fluidly coupled with a chemical cell lysis chamber that is in series or parallel with the electric field cell lysis chamber;
wherein:
a) through f) are in the recited sequence and in successive fluid communication through microfluidic channels; g) through i) are in fluid communication with a microfluidic channel connecting b) and c); and j) is in fluid communication with b).

13. A method for isolating target biomolecules from a sample using the microfluidic recited in claim 12, comprising the steps of:
loading the sample into the sample intake well of the microfluidic cartridge,
moving the sample from the sample intake well to the cell lysis chamber,
lysing the cells in the cell lysis chamber,
moving the cell lysate to the capture and elution chamber,
capturing the target biomolecules on the fluidized solid support,
washing the fluidized solid support with a buffer solution,
eluting the target biomolecules from the fluidized support, and
moving the target biomolecules to the storage chamber.

14. The microfluidic cartridge of claim 1, wherein the one or more insulating members includes a porous membrane, web, or mesh.

15. The micro fluidic cartridge of claim 12, wherein the electric field lysis chamber has an electric field lysis chamber inlet and an electric field lysis chamber outlet that is upstream of and fluidly coupled the inlet conduit, and has an first lysis electrode and second lysis electrode on opposing sides of the electric field lysis chamber with one or more insulating members sandwiched between the first and second lysis electrodes.

16. The microfluidic cartridge of claim 1, wherein the lysing electrode members are configured to lyse the electrically cells with at least 5 V and with a frequency of at least 10 kHz.

17. The microfluidic cartridge of claim 16, wherein the lysing electrode members are optically transparent.

18. The microfluidic cartridge of claim 17, wherein the lysing electrode members are made of optically transparent Indium-Tin-Oxide.

19. The microfluidic cartridge of claim 17, wherein the lysing electrode members are made of optically transparent Indium-Tin-Oxide form a top and bottom surface of the electric field lysis chamber.

20. The microfluidic cartridge of claim 6, wherein the chemical lysis chamber is arranged in series with the electric field lysis chamber.

* * * * *